(12) United States Patent
Koltz, Jr.

(10) Patent No.: US 12,070,546 B2
(45) Date of Patent: Aug. 27, 2024

(54) GAS HEATER FOR SURGICAL GAS DELIVERY SYSTEM WITH GAS SEALED INSUFFLATION AND RECIRCULATION

(71) Applicant: Conmed Corporation, Utica, NY (US)

(72) Inventor: Michael Koltz, Jr., Aurora, CO (US)

(73) Assignee: Conmed Corporation, Largo, FL (US)

( * ) Notice: Subject to any disclaimer, the term of this patent is extended or adjusted under 35 U.S.C. 154(b) by 318 days.

(21) Appl. No.: 17/177,467

(22) Filed: Feb. 17, 2021

(65) Prior Publication Data

US 2022/0233793 A1      Jul. 28, 2022

Related U.S. Application Data

(63) Continuation-in-part of application No. 17/155,572, filed on Jan. 22, 2021, and a continuation-in-part of application No. 17/155,478, filed on Jan. 22, 2021.

(51) Int. Cl.
*A61M 13/00* (2006.01)
*A61B 17/34* (2006.01)

(52) U.S. Cl.
CPC ....... *A61M 13/006* (2014.02); *A61B 17/3474* (2013.01); *A61M 2205/362* (2013.01)

(58) Field of Classification Search
CPC ............ A61B 17/3474; A61M 13/006; A61M 2205/362; A61M 5/44; A61M 5/445; A61M 13/00; A61M 13/003; A61M 2039/0276; A61M 2039/027; A61M 2205/02; A61M 2205/0211; A61M 2205/0233; A61M 2205/0272; A61M 2205/0283; A61M 2205/127; A61M 2205/3368; A61M 2205/36; A61M 2205/3673; A61M 2005/006; A61M 2202/0225; A61M 2205/3653; A61M 16/1075;

(Continued)

(56) References Cited

U.S. PATENT DOCUMENTS

| | | | |
|---|---|---|---|
| 7,854,724 B2 | 12/2010 | Stearns et al. | |
| 8,795,223 B2 | 8/2014 | Stearns et al. | |
| 9,199,047 B2 | 12/2015 | Stearns et al. | |

(Continued)

FOREIGN PATENT DOCUMENTS

JP    2004283475 A    10/2004

OTHER PUBLICATIONS

PCT International Search Report dated May 11, 2022, issued during the prosecution of PCT International Patent Application No. PCT/US2022/012976.

(Continued)

*Primary Examiner* — Kami A Bosworth
*Assistant Examiner* — Avery Smale
(74) *Attorney, Agent, or Firm* — Locke Lord LLP; Scott D. Wofsy

(57) ABSTRACT

A gas heater for a surgical gas delivery system is disclosed, which includes an elongated tubular body defining an interior flow passage having an inlet port for receiving insufflation gas from a gas source and an outlet port for delivering heated insufflation gas to an insufflation manifold, a dielectric support positioned within the interior flow passage of the tubular body, and a resistive element operatively associated with the dielectric support for heating insufflation gas flowing through the tubular body from the inlet port to the outlet port.

16 Claims, 10 Drawing Sheets

(58) Field of Classification Search
CPC ............ A61M 16/108; A61M 16/1085; A61M 16/109; A61M 16/1095
See application file for complete search history.

(56) References Cited

U.S. PATENT DOCUMENTS

| | | |
|---|---|---|
| 9,375,539 B2 | 6/2016 | Stearns et al. |
| 10,384,021 B2 | 8/2019 | Koeth et al. |
| 10,639,434 B2 | 5/2020 | Stearns et al. |
| 10,702,306 B2 | 7/2020 | Silver et al. |
| 2003/0028139 A1 | 2/2003 | Noue |
| 2003/0138244 A1* | 7/2003 | Long .................. F24H 9/2028 392/480 |
| 2011/0194846 A1* | 8/2011 | Wang .................. B82Y 30/00 392/482 |
| 2014/0236074 A1* | 8/2014 | Faif .................... A61M 16/026 604/26 |
| 2015/0048530 A1* | 2/2015 | Cheung ............ A61M 16/0883 261/135 |
| 2015/0202389 A1* | 7/2015 | Stearns ............. B01D 46/0008 604/23 |
| 2015/0359976 A1* | 12/2015 | Richards ................ A61M 5/44 604/113 |
| 2017/0238609 A1* | 8/2017 | Schlipf .................... H05B 3/04 |

OTHER PUBLICATIONS

PCT Written Opinion dated May 11, 2022, issued during the prosecution of PCT International Patent Application No. PCT/US2022/012976.

* cited by examiner

GAS HEATER FOR SURGICAL GAS DELIVERY SYSTEM WITH GAS SEALED INSUFFLATION AND RECIRCULATION

CROSS-REFERENCE TO RELATED APPLICATIONS

The subject application is a continuation-in-part of U.S. application Ser. No. 17/155,478 filed Jan. 22, 2021, and a continuation-in-part of U.S. application Ser. No. 17/155,572 filed Jan. 22, 2021, the disclosures of which are both herein incorporated by reference in their entireties.

BACKGROUND OF THE INVENTION

1. Field of the Invention

The subject invention is directed to minimally invasive surgery, and more particularly, to a gas heater for a surgical gas delivery system used for gas sealed insufflation and recirculation during an endoscopic or laparoscopic surgical procedure.

2. Description of Related Art

Laparoscopic or "minimally invasive" surgical techniques are becoming commonplace in the performance of procedures such as cholecystectomies, appendectomies, hernia repair and nephrectomies. Benefits of such procedures include reduced trauma to the patient, reduced opportunity for infection, and decreased recovery time. Such procedures within the abdominal (peritoneal) cavity are typically performed through a device known as a trocar or cannula, which facilitates the introduction of laparoscopic instruments into the abdominal cavity of a patient.

Additionally, such procedures commonly involve filling or "insufflating" the abdominal cavity with a pressurized fluid, such as carbon dioxide, to create an operating space, which is referred to as a pneumoperitoneum. The insufflation can be carried out by a surgical access device, such as a trocar, equipped to deliver insufflation fluid, or by a separate insufflation device, such as an insufflation (veress) needle. Introduction of surgical instruments into the pneumoperitoneum without a substantial loss of insufflation gas is desirable, in order to maintain the pneumoperitoneum.

During typical laparoscopic procedures, a surgeon makes three to four small incisions, usually no larger than about twelve millimeters each, which are typically made with the surgical access devices themselves, often using a separate inserter or obturator placed therein. Following insertion, the obturator is removed, and the trocar allows access for instruments to be inserted into the abdominal cavity. Typical trocars provide a pathway to insufflate the abdominal cavity, so that the surgeon has an open interior space in which to work.

The trocar must also provide a way to maintain the pressure within the cavity by sealing between the trocar and the surgical instrument being used, while still allowing at least a minimum amount of freedom of movement for the surgical instruments. Such instruments can include, for example, scissors, grasping instruments, and occluding instruments, cauterizing units, cameras, light sources and other surgical instruments. Sealing elements or mechanisms are typically provided on trocars to prevent the escape of insufflation gas from the abdominal cavity. These sealing mechanisms often comprise a duckbill-type valve made of a relatively pliable material, to seal around an outer surface of surgical instruments passing through the trocar.

SurgiQuest, Inc., a wholly owned subsidiary of ConMed Corporation has developed unique gas sealed surgical access devices that permit ready access to an insufflated surgical cavity without the need for conventional mechanical valve seals, as described, for example, in U.S. Pat. Nos. 7,854,724 and 8,795,223. These devices are constructed from several nested components including an inner tubular body portion and a coaxial outer tubular body portion. The inner tubular body portion defines a central lumen for introducing conventional laparoscopic or endoscopic surgical instruments to the surgical cavity of a patient and the outer tubular body portion defines an annular lumen surrounding the inner tubular body portion for delivering insufflation gas to the surgical cavity of the patient and for facilitating periodic sensing of abdominal pressure.

SurgiQuest has also developed multimodal surgical gas delivery systems for use with the unique gas sealed access devices described above. These gas delivery systems, which are disclosed for example in U.S. Pat. Nos. 9,199,047 and 9,375,539 have a first mode of operation for providing gas sealed access to a body cavity, a second mode of operation for performing smoke evacuation from the body cavity, and a third mode of operation for providing insufflation gas to the body cavity.

Intraoperative hypothermia can occur in laparoscopic surgical procedures, resulting in postoperative complications and prolonged recovery time. Active warming methods used to prevent intraoperative hypothermia include forced air warming systems, warmed ventilator circuits and warmed intravenous and irrigation fluids. The use of warmed surgical gas to establish pneumoperitoneum during laparoscopy has been associated with reduced incidence of intraoperative hypothermia.

Indeed, the SurgiQuest multimodal gas delivery system described above employs a heating mechanism in the form of a thick-walled brass fitting with an RF resistor that transfers heat to surgical gas as it enters the system from a gas source. However, the heat transfer volume of that fitting is relatively small and the transit time through the fitting to facilitate heat transfer to the gas flow is relatively short. Thus, an improved gas heater without these limitations would be beneficial.

SUMMARY OF THE DISCLOSURE

The subject invention is directed to a new and useful gas heater for a multimodal surgical gas delivery system used for gas sealed insufflation and recirculation during an endoscopic or laparoscopic surgical procedure. The gas heater includes an elongated tubular body defining an interior flow passage having an inlet port for receiving insufflation gas from a gas source and an outlet port for delivering heated insufflation gas to an insufflation manifold. The tubular body may be formed from a material that facilitates UVC sterilization of the gas flowing therethrough, such as, for example, UVC transparent quartz glass.

A dielectric support is positioned within the interior flow passage of the tubular body, and a resistive element is operatively associated with the dielectric support for transferring heat to insufflation gas flowing through the tubular body from the inlet port to the outlet port. In one embodiment of the subject invention, the dielectric support is an elongated support beam that has a ribbed exterior surface and the resistive element is wrapped around the ribbed exterior surface of the support beam. In another embodiment of the subject invention, the dielectric support is an elongated support tube and the resistive element is partially wrapped around an exterior surface of the support tube and partially woven transversely through an interior bore of the support tube.

The dielectric support is preferably formed from a ceramic material and the resistive element is preferably formed from a nickel based alloy. The gas heater further includes a first sensing port for accommodating a first heat sensor adjacent the inlet port to measure an inlet gas temperature and a second sensing port for accommodating a second heat sensor adjacent the outlet port to measure an outlet gas temperature. The gas heater also includes electrical couplings for connecting the resistive element to an electrical energy source.

The subject invention is also directed to a surgical gas delivery system that includes a source of insufflation gas, a pressure regulator for receiving insufflation gas from the source, an insufflation manifold for receiving pressure regulated insufflation gas from the pressure regulator for delivery to one or more surgical access ports communicating with the gas delivery system, and a gas heater as described above for heating the insufflation gas received by the insufflation manifold. The gas delivery system further includes a gaseous sealing manifold for communicating with a gas sealed access port and wherein the outlet port of the gas heater communicates with the gaseous sealing manifold in parallel with the insufflation manifold.

These and other features of the gas heater and the gas delivery system of the subject invention will become more readily apparent to those having ordinary skill in the art to which the subject invention appertains from the detailed description of the preferred embodiments taken in conjunction with the following brief description of the drawings.

BRIEF DESCRIPTION OF THE DRAWINGS

So that those skilled in the art will readily understand how to make and use the gas heater and gas delivery system of the subject invention without undue experimentation, preferred embodiments thereof will be described in detail herein below with reference to the figures wherein.

DETAILED DESCRIPTION OF THE PREFERRED EMBODIMENTS

Figure 1:
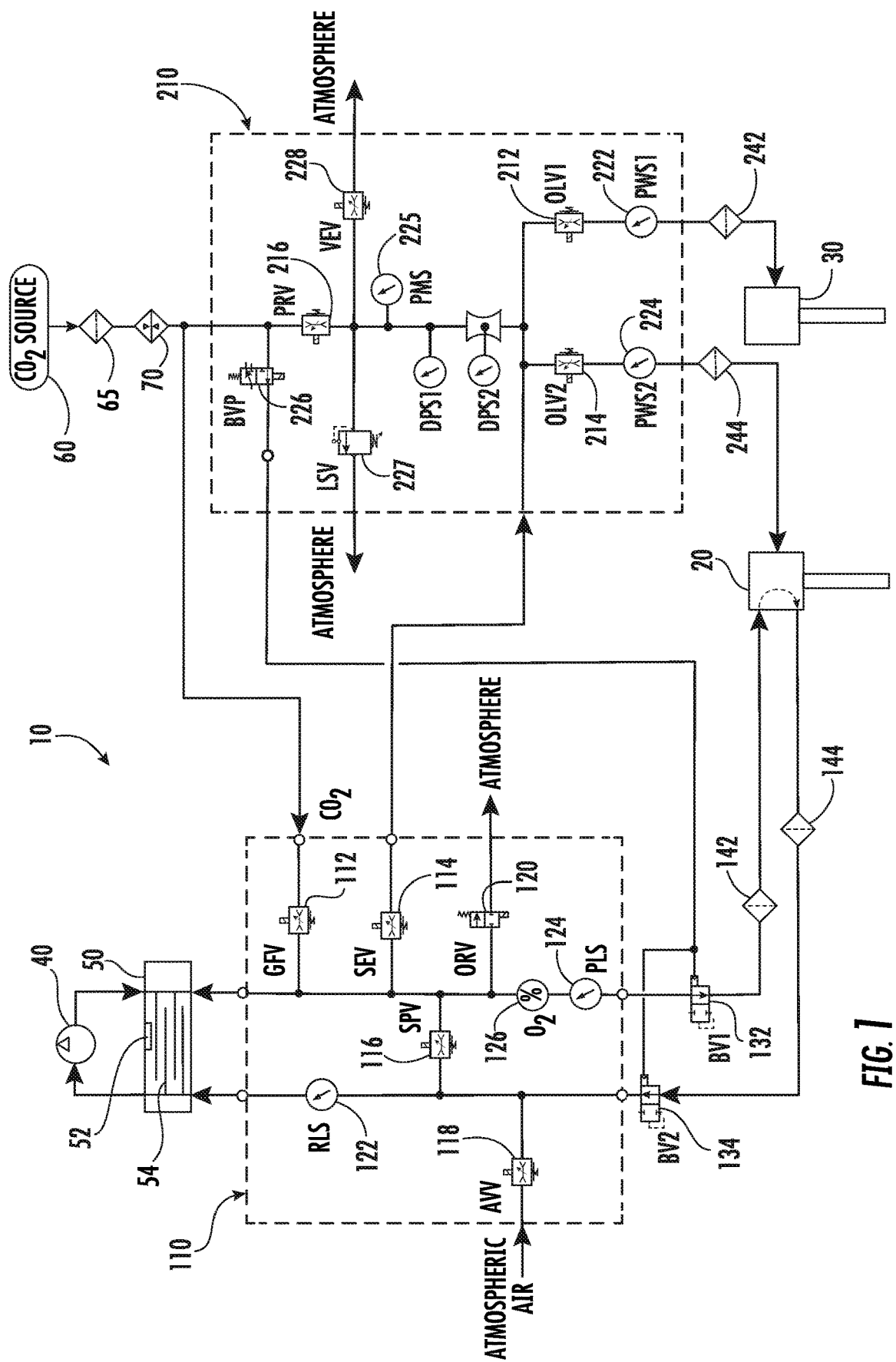
FIG. 1 is a schematic diagram of the multi-modal gas delivery system of the subject invention, which includes a gaseous sealing manifold for communicating with a gas sealed access port and an insufflation manifold for communicating with the gas sealed access port and with a valve sealed access port, wherein the gas delivery system includes a gas heater for transferring heat to surgical gas entering the system from a gas source.

Referring now to the drawings wherein like reference numerals identify similar structural elements and features of the subject invention, there is illustrated in FIG. 1 a new and useful multi-modal surgical gas delivery system 10 that is adapted and configured for gas sealed insufflation, recirculation and smoke evacuation during an endoscopic or laparoscopic surgical procedure. The multi-modal surgical gas delivery system 10 of the subject invention includes a gaseous sealing manifold 110 for communicating with a gas sealed access port 20 and an insufflation manifold 210 for communicating with the gas sealed access port 20 and with a valve sealed access port 30.

The gas sealed access port 20 is of the type disclosed in commonly assigned U.S. Pat. No. 8,795,223, which is incorporated herein by reference. The gas sealed access port 20 is adapted and configured to provide gas sealed instrument access to a body cavity, while maintaining a stable pressure within the body cavity (e.g., a stable pneumoperitoneum in the peritoneal or abdominal cavity). In contrast, the valve sealed access port 30 is a conventional or standard trocar, for providing access to a body cavity through a mechanical valve seal, such as, for example, a duckbill seal, septum seal or the like. Depending upon the requirements of a particular surgical procedure, the multi-modal gas delivery system 10 can be utilized with either the gas sealed access port 20, the valve sealed access port 30 or with both access ports 20, 30 at the same time.

The gas delivery system 10 further includes a compressor or positive pressure pump 40 for recirculating surgical gas through the gas sealed access port 20 by way of the gaseous sealing manifold 110. The compressor 40 is preferably driven by a brushless DC (direct-current) motor, which can be advantageously controlled to adjust gas pressure and flow rates within the gas delivery system 10, as disclosed for example in commonly assigned U.S. Pat. No. 10,702,306, which is incorporated herein by reference. Alternatively, the compressor 40 can be driven by an AC motor, but a DC motor will be relatively smaller and lighter, and therefore more advantageous from a manufacturing standpoint.

An intercooler and/or condenser 50 is operatively associated with the compressor 40 for cooling or otherwise conditioning gas recirculating through the gaseous sealing manifold 110. A UVC irradiator 52 is operatively associated with the intercooler or condenser 50 for sterilizing gas recirculating through the internal flow passages 54 formed therein by way of the compressor 40. In addition, the UVC irradiator 52 is intended to sterilize the interior surfaces of the gas conduits or flow passages 54 through which the gas flows within the intercooler/condenser 50.

The UVC irradiator preferably includes at least one LED light source or a florescent light source that is adapted and configured to generate UVC radiation at a wavelength of about between 240-350 nm, and preferably about 265 nm. This ultraviolet light at such a wavelength can sterilize viral, bacterial and microbial bodies within the gas conduits of the system, and can reduce coronavirus including SARS-COV-2.

Preferably, compressor 40, intercooler/condenser 50, gaseous sealing manifold 110 and insufflation manifold 210 are all enclosed within a common housing, which includes a graphical user interface and control electronics, as disclosed for example in commonly assigned U.S. Pat. No. 9,199,047, which is incorporated herein by reference.

The gas delivery system 10 further includes a surgical gas source 60 that communicates with the gaseous sealing manifold 110 and the insufflation manifold 210. The gas source 60 can be a local pressure vessel or a remote supply tank associated with a hospital or healthcare facility. Preferably, gas from the surgical gas source 60 flows through a high pressure regulator 65 and a gas heater 70 before it is delivered to the gaseous sealing manifold 110 and the insufflation manifold 210. Preferably, the high pressure regulator 65 and the gas heater 70 are also enclosed with the compressor 40, intercooler 50, gaseous sealing manifold 110 and insufflation manifold 210 in the common housing. Two embodiments of the gas heater 70 will be described in greater detail below with reference to FIGS. 2 through 12.

The gas delivery system 10 further includes a first outlet line valve (OLV1) 212 that is operatively associated with the insufflation manifold 210 for controlling a flow of insufflation gas to the valve sealed access port 30 and a second outlet line valve (OLV2) 214 that is operatively associated with the insufflation manifold 210 for controlling a flow of insufflation gas to the gas sealed access port 20.

In accordance with a preferred embodiment of the subject invention, the first and second outlet line valves 212, 214 of insufflation manifold 210 are proportional valves that are configured to dynamically alter or otherwise control the outflow of insufflation gas to the access ports 20, 30 to match volume fluctuations that may arise in a patient's body cavity as they occur. The first and second proportional outlet line valves 212, 214 provide the gas delivery system 10 with fine control of insufflation gas flow rate to achieve stable flow rates at lower pressure, reduce pressure oscillation and eliminate pneumatic hammer.

Because the first and second proportional outlet line valves 212, 214 are proximal to the patient where flow friction losses are relatively low, the gas delivery system 10 is able to measure peritoneal pressures accurately. Moreover, the use of proportional outlet line valves for this purpose is uniquely possible here, because there is constant gas recirculation throughout the gas delivery system 10, either by way of closed loop smoke evacuation or by way of the gas sealed access port 20.

Proportional valves allow for infinitely variable gas flow adjustment between a minimum flow state and a maximum flow state. Given that some volume changes in a patient's body cavity, such as breathing, are expected and consistent, by employing proportional outlet line valves, the insufflation manifold 210 is able to dynamically alter the gas flow to the body cavity to inverse the expected volume changes, resulting in a neutral effect on the pressure inside the cavity.

An additional benefit of using proportional valves for controlling the outflow of insufflation gas from manifold 210 is a reduction in response time, as compared to that of a solenoid valve. A solenoid valve operates by applying energy to coils, which produces an electromagnetic force that moves a piston. However, the energizing of the coils takes some amount of time, introducing a delay between a commanded action and the physical movement of the piston. In contrast, proportional valves, as employed in the gas delivery system 10 of the subject invention, do not have an energization delay in general, and so they have an improved response time as compared to solenoid valves.

The insufflation manifold 210 further includes a first patient pressure sensor (PWS1) 222 downstream from the first outlet line valve 212 and a second patient pressure sensor (PWS1) 224 downstream from the second outlet line valve 214. These two patient pressure sensors are used to measure abdominal pressure to control outlet line valves 212, 214, respectively. Two other pressure sensors are located upstream from the outlet line valves 212, 214, and are labeled as DPS1 and DPS2. These two pressure sensors are situated within a venturi to measure a pressure differential that is used to infer a total gas flow rate from the insufflation manifold 210 to the patient's body cavity.

A primary proportional valve (PRV) 216 is also operatively associated with insufflation manifold 210 and it is located upstream from the first and second outlet line valves 212, 214 to control the flow of insufflation gas to the first and second outlet line valves 212, 214. Proportional valve 216 functions to maintain an intermediate pressure within the insufflation manifold 210 (as the central node in the LPU) at a constant pressure between 1 and 80 mmHg, dependent on the system operating mode. The opening of PRV 216 can be indirectly initiated by any of the following actions: patient respiration, gas leakage downstream of PRV 216, or the opening of the safety valve LSV 227 or ventilation valve VEV 228, i.e. any event that causes an intermediate pressure to drop. In the system. LSV 227 and VEV 228 are described in more detail below.

The gaseous sealing manifold 110 also includes a high pressure gas fill valve (GFV) 112 that is operatively associated with an outlet side of the compressor 40. GFV 112 is adapted and configured to control gas delivered into the gaseous sealing manifold 110 from the source of surgical gas 60. Preferably, the gas fill valve 112 is a proportional valve that is able to dynamically control surgical gas delivered into the gaseous sealing manifold 110.

The gaseous sealing manifold 110 also includes a smoke evacuation valve (SEV) 114 that is operatively associated with an outlet side of the compressor 40 for dynamically controlling gas flow between the gaseous sealing manifold 110 and the insufflation manifold 210 under certain operating conditions, such as, for example, when the gas delivery device 10 is operating in a smoke evacuation mode. Preferably, the smoke evacuation valve 114 is a proportional valve.

A bypass valve (SPV) 116 is positioned between an outlet side of the compressor 40 and an inlet side of the compressor 40 for controlling gas flow within the gaseous sealing manifold 110 under certain operating conditions. Preferably, the bypass valve 116 is a proportional valve, which is variably opened to establish and control the gaseous seal generated within gas sealed access port 20. Moreover, bypass valve 116 controls gas flow rate to the gaseous seal using feedback from pressure sensors 122, 124, described in further detail below.

The gaseous sealing manifold 110 also includes an air ventilation valve (AVV) 118, which is operatively associated with an inlet side of the compressor 40 for controlling the entrainment of atmospheric air into the system 10 under certain operating conditions. For example, AVV 118 will permit the introduction of atmospheric air into the gaseous sealing circuit to increase the air mass (i.e., the standard volume) within the circuit. The thermodynamics of clinical use conditions can cause a loss of standard volume within the gas circuit. The ventilation valve 118 permits the gas delivery system 10 to make up for this lost volume, in order to ensure that pump pressure and flow rates are sufficient to maintain the gaseous seal within the gas sealed access port 20. The ventilation valve 118 can also be opened to reduce the vacuum side pressure in the gas seal circuit.

An overpressure relief valve (ORV) 120 is operatively associated with an outlet side of the compressor 40 for controlling a release of gas from the system 10 to atmosphere under certain operating conditions. Preferably, the overpressure relief valve 120 is a proportional valve that is opened to reduce the positively pressurized side of the gas seal circuit, especially in the event of an emergency, such as a loss of power to the gas delivery system 10. The normally open configuration of relief valve 120 reduces the risk of over-pressurization of the patient cavity upon loss of power to that valve.

A first pressure sensor (RLS) 122 is operatively associated with an inlet side of the compressor 40 and a second pressure sensor (PLS) 124 is operatively associated with an outlet side of the compressor 40. These pressure sensors 122, 124 are situated to have unobstructed and minimally restricted commutation with the patient's abdominal cavity in order to continuously and accurately measure cavity pressure. The signals from these two pressure sensors 122, 124 are employed by a controller of the gas delivery system 10 to modulate the opening of the two outlet line valves 212 and 214, to control the patient cavity pressure.

In addition, the gaseous sealing manifold 110 includes a gas quality sensor 126 that is operatively associated with an outlet side of the compressor 40. The gas quality sensor monitors the level of oxygen in the recirculation circuit, which corresponds to a concentration of $CO_2$ in the body cavity of a patient, as disclosed in U.S. Pat. No. 9,199,047.

A first blocking valve (BV1) 132 is operatively associated with an outlet flow path of the gaseous sealing manifold 110 and a second blocking valve (BV2) 134 is operatively associated with an inlet flow path to the gaseous sealing manifold 110. The blocking valves 132, 134 are employed during a self-test prior to a surgical procedure, as disclosed in U.S. Pat. No. 9,199,047. It is envisioned that the first and second blocking valves 132, 134 could be are mechanically actuated or pneumatically actuated.

A first filter element 142 is positioned downstream from the first blocking valve 132 for filtering pressurized gas flowing from the compressor 40 to the gas sealed access port 20, and a second filter element 144 is positioned upstream from the second first blocking valve 134 for filtering gas returning to the compressor 40 from the gas sealed access port 20. Preferably, the filter elements 142, 144 are housed within a common filter cartridge, as disclosed for example in U.S. Pat. No. 9,199,047.

The first and second blocking valves 132, 134 communicate with a blocking valve pilot (BVP) 226 that is included within with the insufflation manifold 210. Preferably, the blocking valve pilot 226 is a solenoid valve. It is envisioned that BVP 226 could be fed from the compressor outlet as shown or from a gas source such of surgical gas or air. The insufflation manifold 110 further includes a pressure sensor (PMS) 225 located downstream from the primary proportional valve 216 and upstream from the outlet line valves 212, 214. The two outlet line valves are opened to introduce insufflation gas to the patient's body cavity by way of the access ports 23, 30. This introduction of gas has the effect of increasing pressure within the body cavity. Additionally, the outlet line valves 212, 214 can be opened in conjunction with air ventilation valve 228 to release gas from the body cavity, having the effect of desufflation and reduction of cavity pressure.

The insufflation manifold 210 further includes a low pressure safety valve (LSV) 227 downstream from the primary proportional valve 216 and upstream from the first and second outlet line valves 212, 214 for controlling a release of gas from the system 10 to atmosphere under certain operating conditions. LSV 227 is a purely mechanical valve that functions to limit the maximum intermediate pressure within the manifold 210 or LPU (Low Pressure Unit) in the event of a power interruption, a pressure controller malfunction or if a valve located upstream from the LSV sticks in an open position.

In addition, a ventilation exhaust valve (VEV) 228 is positioned downstream from the primary proportional valve 216 and upstream from the outlet line valves 212, 214 for controlling a release of gas from the system 10 to atmosphere under certain operating conditions. The ventilation exhaust valve 228 is a preferably a proportional valve that is opened to desufflate or otherwise reduce patient cavity pressure. Additionally, VEV 228 can be opened to reduce intermediate pressure within the LPU.

Figure 2:
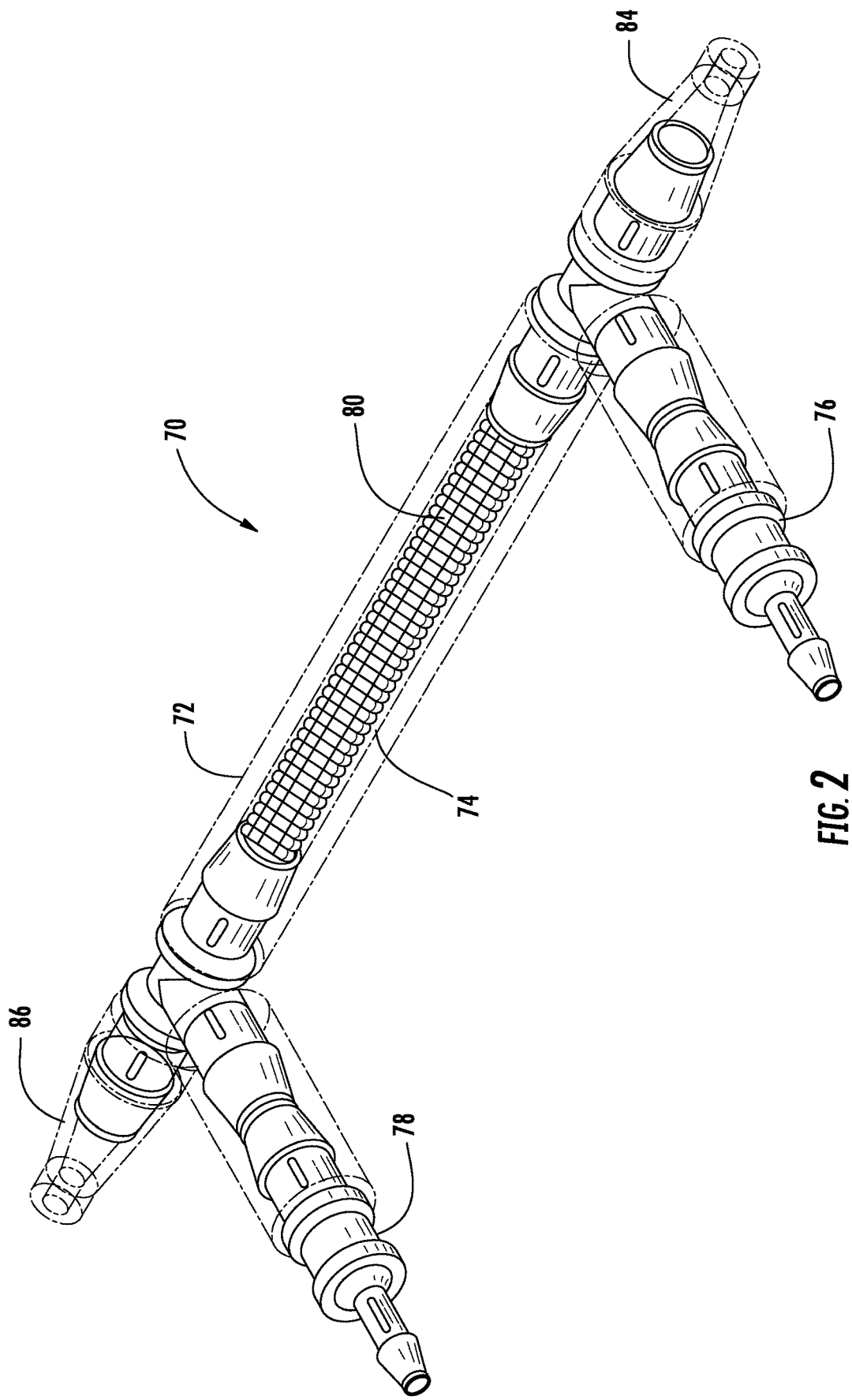
FIG. 2 is a perspective view of the gas heater of the subject invention.
Figure 3:
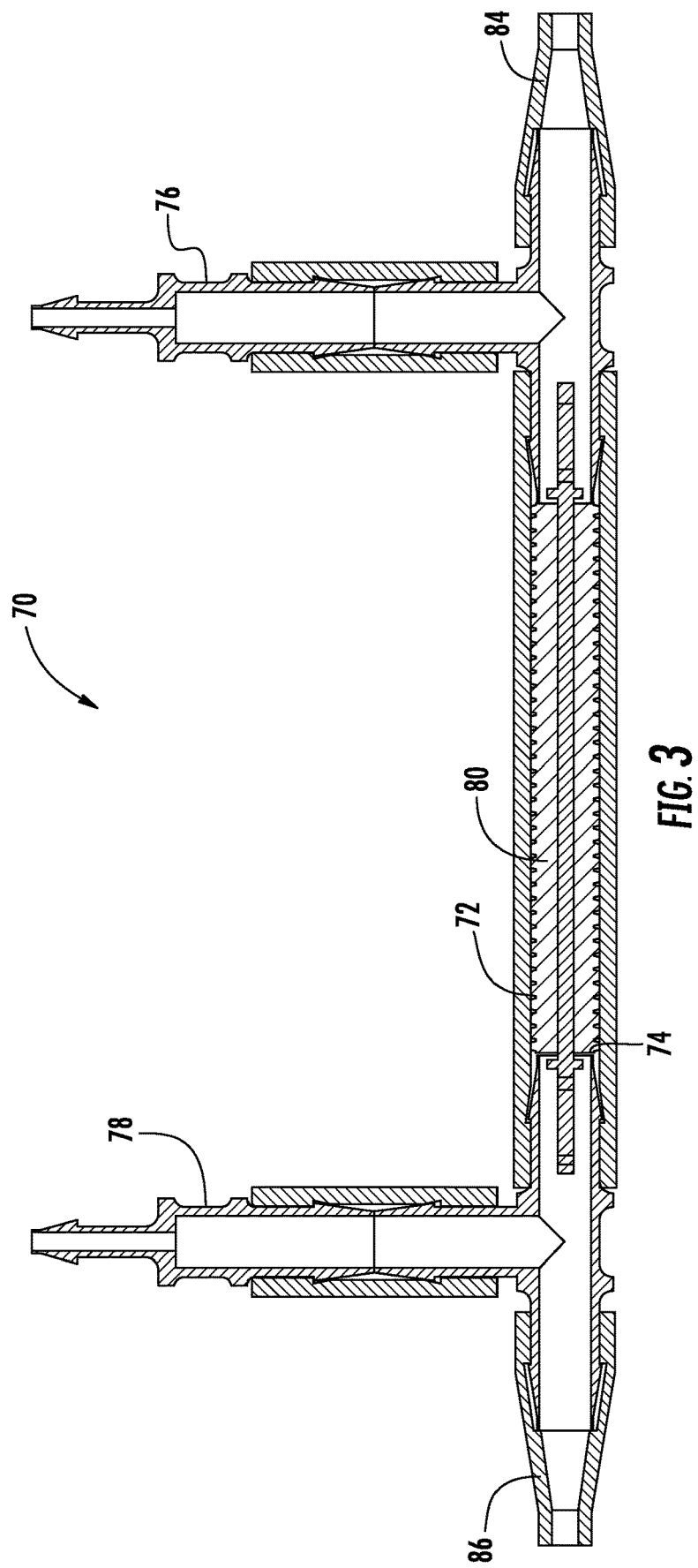
FIG. 3 is a top plan view of the gas heater shown in FIG. 2.

A filter element 242 is positioned downstream from the first outlet line valve 212 for filtering insufflation gas flowing from the insufflation manifold 210 to the valve sealed access port 30. Another filter element 244 is positioned downstream from the second outlet line valve 224 for filtering insulation gas flowing from the insufflation manifold 210 to the gas sealed access port 20. Preferably, filter element 244 is housed with filter elements 142 and 144 in a common filter cartridge, while filter element 242 is separately located. Referring now to FIGS. 2 and 3, there is illustrated the gas heater 70 of the subject invention, which includes an elongated tubular body 72 defining an interior flow passage 74 having an inlet port 76 for receiving insufflation gas from the gas source 60 and an outlet port 78 for delivering heated insufflation gas to the gaseous sealing manifold 110 and the insufflation manifold 210, as shown schematically in FIG. 1. The tubular body 72 is formed from a UVC transparent quartz glass so as to permit an external UVC source (not shown) to sterilize the insufflation gas passing through the heater 70. The inlet port 76 and outlet port 78 extend perpendicular to the longitudinal axis of the tubular body 72.

Figure 4:
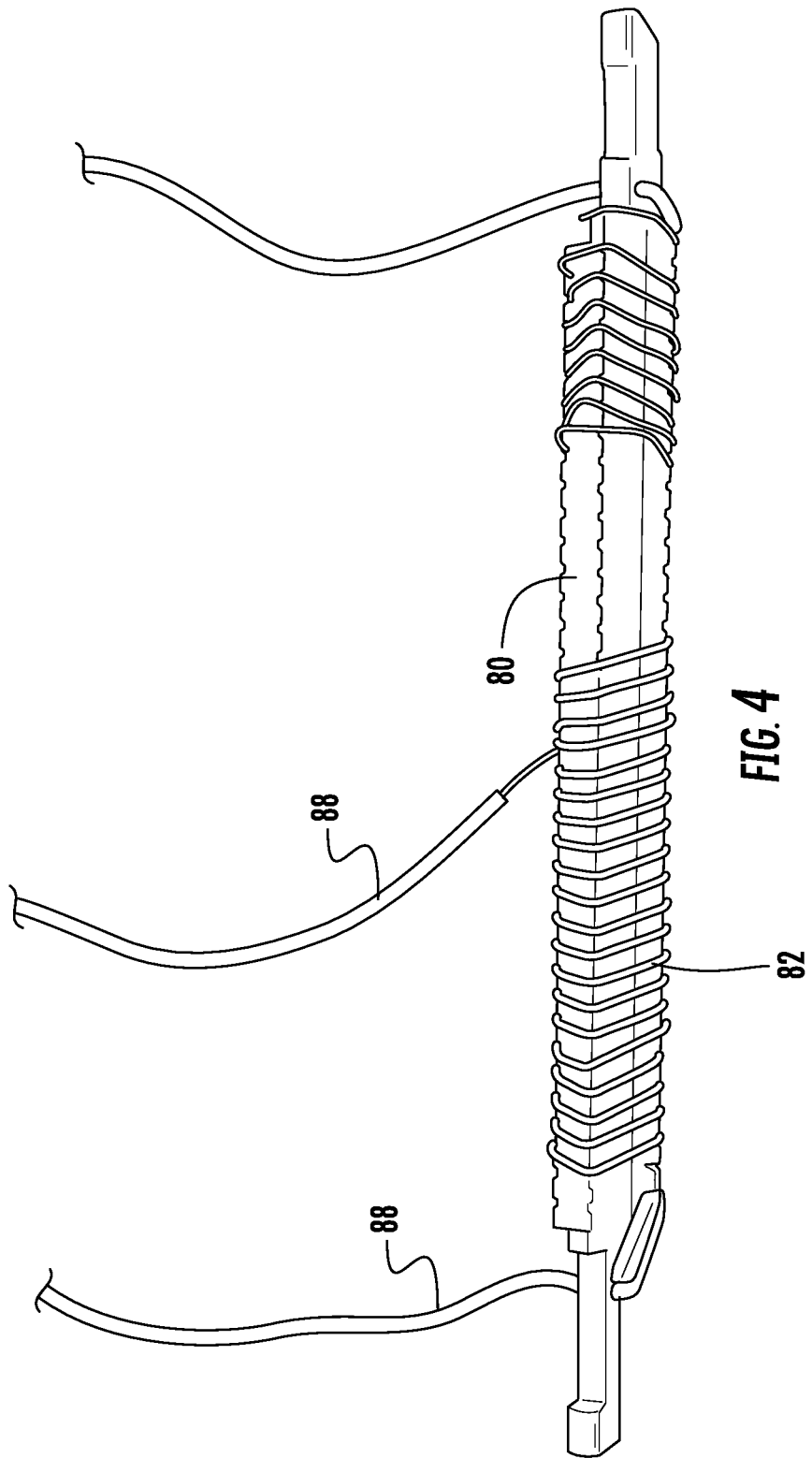
FIG. 4 depicts the dielectric support beam and resistive element of the gas heater shown in FIG. 2.
Figure 5:
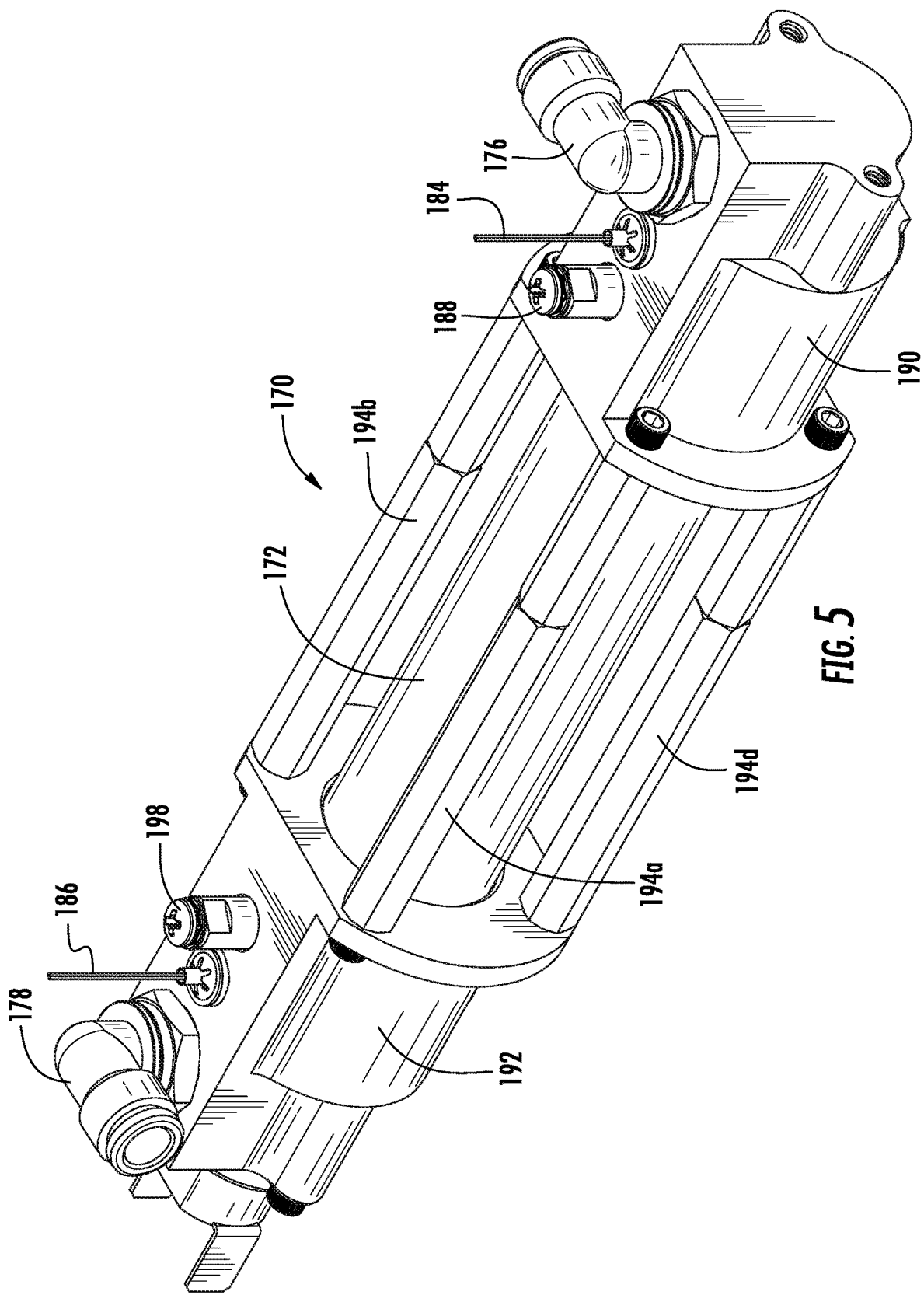
FIG. 5 is a perspective view of another embodiment of the gas heater of the subject invention.
Figure 6:
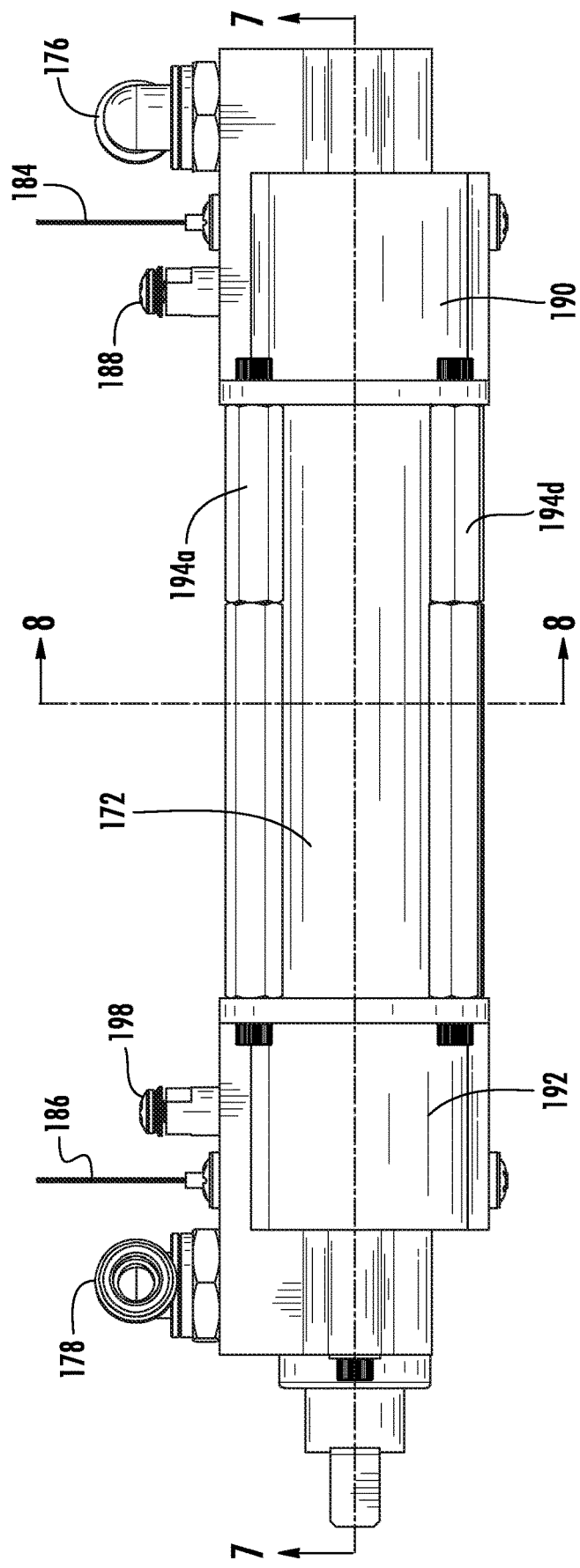
FIG. 6 is a side elevational view of the gas heater shown in FIG. 5.

A ribbed dielectric support beam 80 extends coaxially through the interior flow passage 74 of the tubular body 72, and a resistive element 82 is wrapped around or otherwise associated with the ribbed support beam 80, as shown in FIG. 4, for transferring heat to insufflation gas flowing through the tubular body 72 from the inlet port 76 to the outlet port 78. The elongated tubular body 72 provides a greater amount of heat transfer volume and longer transit time to facilitate heat transfer from the resistive element 82 to the gas flow, as compared to the prior art resistive heater described hereinabove.

The gas flow rate through the tubular body 72 of heater 70 is about 50 slpm but it can range between 0 and 100 slpm. The maximum heat power transfer into the gas flowing through the tubular body 72 of heater 70 is about 190 Watts, but it could range between 25 and 1000 Watts depending on the dimensional scale of the heater assembly.

In accordance with a preferred embodiment of the subject invention, the dielectric support beam 80 is formed from at least in part from a ceramic material. Alternatively, the support beam 80 can be formed from a ceramic-thermoset polymer composite or the like. The resistive element is 82 is preferably formed from a nickel based alloy, such as, for example Nichrome or the like. Electrical couplings or conductors 88 are associated with the support beam 80 for connecting the resistive element 82 to an electrical energy source, as shown in FIG. 4.

While the resistive element 82 is illustrated, by way of example, as a resistive wire, it is envisioned that the resistive element 82 could take the form of foil, laminates, printed inks, and/or wire mesh. In any case, the total end-to-end resistance of the resistive element 82 is preferably about 3 ohms, but it could range between 0.1 ohm and 100 ohms. The resistance per unit length of the resistive element 82 is preferably about 1 ohm per foot, but it could range between 1 milli-ohm per foot and 1 kilo-ohm per foot. It is further envisioned that the resistive element 82 could be comprised of multiple resistive elements that are connected in series, in parallel, or in combinations thereof.

Referring back to FIGS. 2 and 3, the tubular body 72 of the gas heater 70 includes a first sensing port 84 adjacent the inlet port 76 for accommodating a first heat sensor (not shown) to measure an inlet gas temperature and a second sensing port 86 adjacent the outlet port 78 for accommodating a second heat sensor (not shown) to measure an outlet gas temperature. The first sensing port 76 and the second sensing port 78 are aligned with the longitudinal axis of the tubular body 72.

Referring now to FIGS. 5 through 10, there is illustrated another embodiment of the gas heater of the subject invention, which is designated generally by reference numeral 170. Gas heater 170 includes an elongated tubular body 172 supported between two end caps 190 and 192. The tubular body 172 of gas heater 170 is preferably formed from UVC transparent quartz glass and it defines an internal flow passage 174 (see FIG. 7). The two end caps 190 and 192 are joined or otherwise fastened together by four elongated spacer struts 194a-194d.

Figure 7:
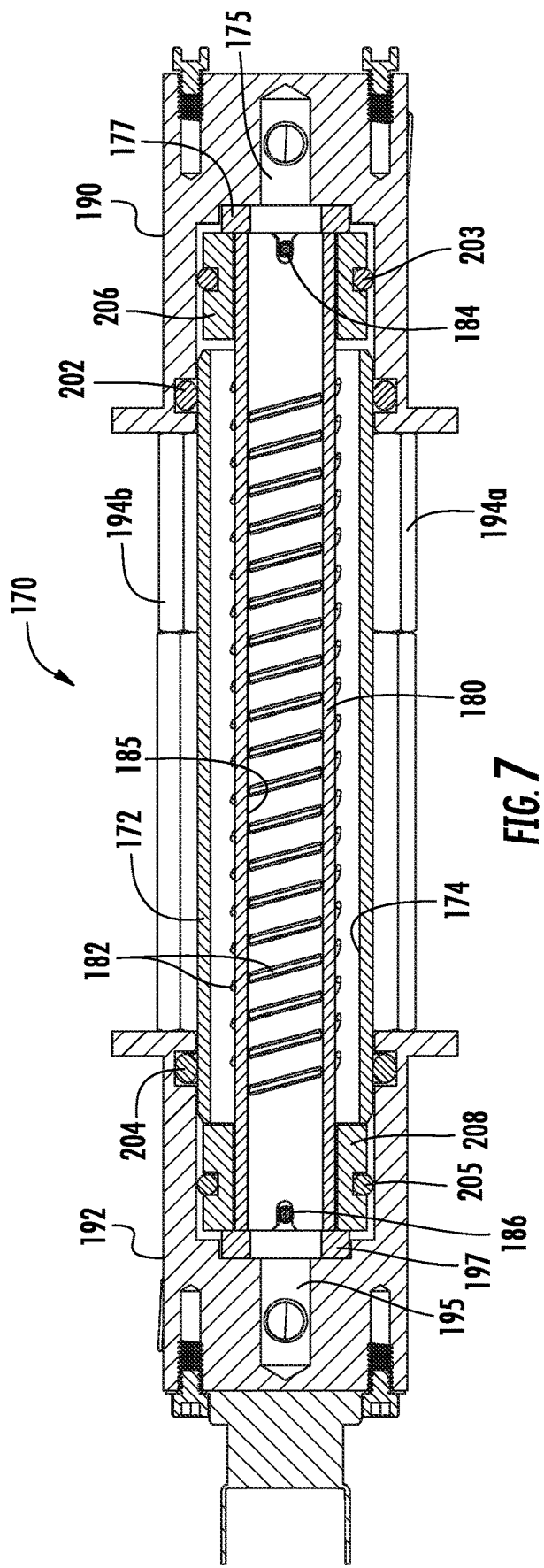
FIG. 7 is a cross-sectional view taken along line 7-7 of FIG. 6.
Figure 10:
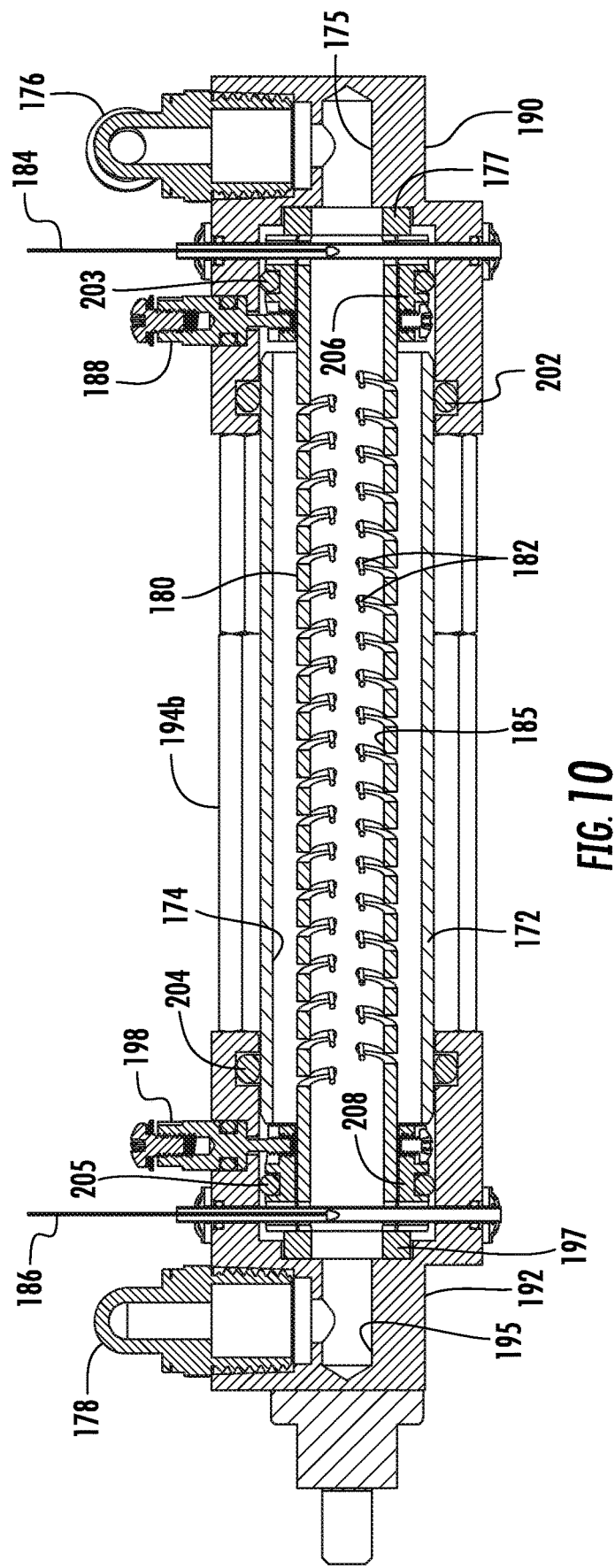
FIG. 10 is a cross-sectional view taken along line 10-10 of FIG. 9.

An inlet port 176 in the form of a right-angled connective fitting is operatively associated with end cap 190 and an outlet port 178 in the form of an oppositely directed right-angled connective fitting is operatively associated with end cap 192. As best seen in FIGS. 7 and 10, the inlet port 176 communicates with an inlet flow passage 175 formed in end cap 190, which communicates with the internal flow passage 174 of tubular body 172 through a spacer ring 177. Similarly, the outlet port 178 communicates with an outlet flow passage 195 formed in end cap 192, which communicates with the internal flow passage 174 of tubular body 172 through a spacer ring 197.

With continuing reference to FIGS. 7 and 10, an O-ring 202 is seated in end cap 190 for sealingly engaging the outer surface of the tubular body 172 disposed therein, and another O-ring 204 is seated in end cap 192 for sealingly engaging the outer surface of the tubular body 172 disposed therein. A dielectric support tube 180 extends coaxially through the interior flow passage 174 of tubular body 172. The support tube 180 is formed from a ceramic material, such as for example, a ceramic-thermoset polymer composite or the like.

An inlet end of support tube 180 is retained within end cap 190 by a bushing 206 and an O-ring 203 seated on bushing 206. An outlet end of support tube 180 is retained within end cap 192 by a bushing 208 and an O-ring 205 seated on bushing 208. Spacer rings 177 and 197, as well as O-rings 203 and 205 act as thermal insulators to limit heat transfer between the support tube 180 and the end caps 190 and 192 of gas heater 170.

Figure 8:
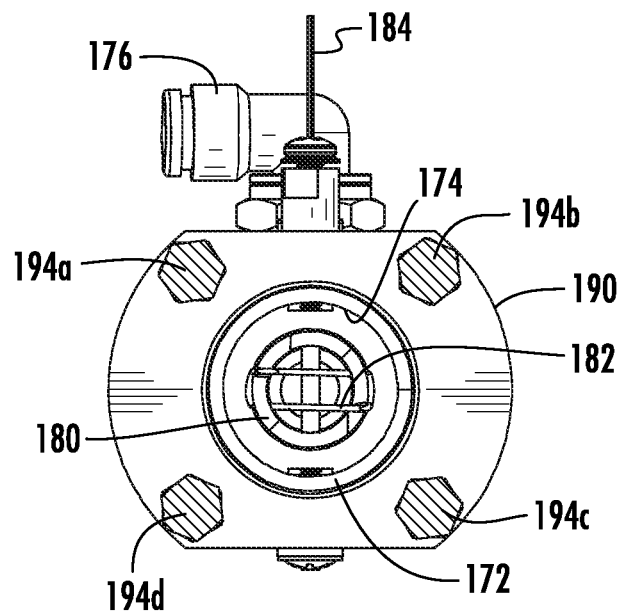
FIG. 8 is a cross-sectional view taken along line 8-8 of FIG. 6.
Figure 9:
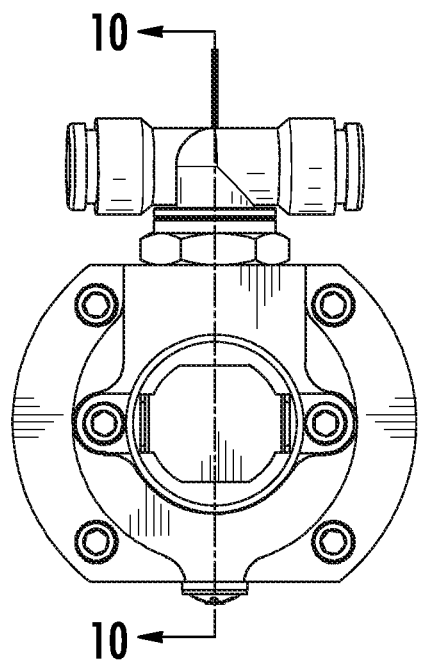
FIG. 9 is an end view of the gas heater shown in FIG. 5.
Figure 11:
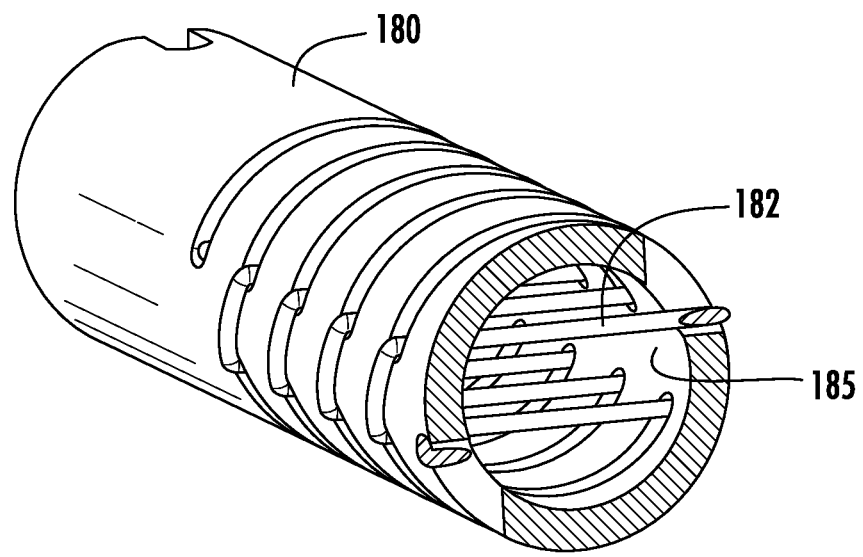
FIG. 11 is a partial perspective view of the dielectric support tube of the gas heater shown in FIG. 5, wherein the resistive element is located internally and oriented substantially transverse to the direction of net gas flow through the gas heater.
Figure 12:
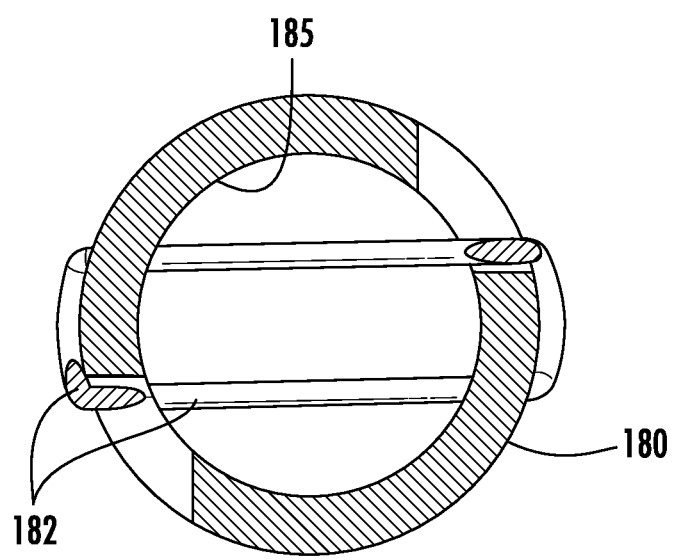
FIG. 12 is an end view of the section of the dielectric support tube shown in FIG. 11.

A resistive element 182 is operatively associated with the support tube 180. The resistive element is 182 is preferably formed from a nickel based alloy, such as, for example Nichrome or the like. As best seen in FIGS. 8, 11 and 12, the resistive element 182 is located both on the exterior surface of the support tube 180 and within the interior bore 185 of the support tube 180 spaced away from interior wall thereof.

More specifically, the resistive element 182 is wrapped partially around the exterior surface of the support tube 180 and woven through the interior bore 185 of the support tube 180. In this orientation, the resistive element 182 is substantially transverse to the direction of net gas flow through the tubular body 172 of the gas heater 170. This facilitates heat transfer between the resistive element 182 and the gas flowing through the tubular body 172 by converting laminar flow into turbulent flow.

A first sensing probe 184 is associated with end cap 190, located adjacent the inlet port 176, for measuring an inlet gas temperature. A second sensing probe 186 is associated with end cap 192, located adjacent the outlet port 178, for measuring an outlet gas temperature. The first and second sensing probes 184, 186 extend perpendicular to the longitudinal axis of the tubular body 172, and intersect the bore 185 of tubular support beam 180, as best seen in FIG. 10. A first electrical coupling 188 is associated with end cap 190 and a second electrical coupling 198 is associated with end cap 192. Electrical coupling 188 and 198 are adapted and configured to provide a connection between the resistive element 182 and an electrical power source, by way of appropriate conductive wires (not shown).

While the gas delivery system and gas heater of the subject disclosure has been shown and described with reference to preferred embodiments, those skilled in the art will readily appreciate that changes and/or modifications may be made thereto without departing from the scope of the subject disclosure.

What is claimed is:

1. A gas heater for a surgical gas delivery system comprising:
    a) an elongated tubular body defining an interior flow passage having an inlet port for receiving insufflation gas from a gas source and an outlet port for delivering heated insufflation gas to an insufflation manifold;
    b) a dielectric support positioned within the interior flow passage of the elongated tubular body, wherein the dielectric support is an elongated support tube defining a longitudinal axis and having an interior bore bounded by a tubular wall having an exterior surface and an interior surface, and wherein two sets of longitudinally spaced apart and diametrically opposed arcuate slots extend through the tubular wall of the elongated support tube from the exterior surface thereof to the interior surface thereof; and
    c) a resistive element operatively associated with the dielectric support for heating the insufflation gas flowing through the elongated tubular body from the inlet port to the outlet port, wherein the resistive element is partially wrapped around the exterior surface of the elongated support tube and partially woven through the arcuate slots in the tubular wall of the elongated support tube, such that the resistive element extends through the interior bore of the elongated support tube_to form two parallel sets of interconnected axially spaced apart sections within the interior bore of the elongated support tube that are oriented substantially transverse to the longitudinal axis of the elongated support tube and to a direction of net gas flow through the elongated tubular body.

2. The gas heater of claim 1, wherein the dielectric support is formed at least in part from a ceramic material.

3. The gas heater of claim 2, wherein the dielectric support is formed from a ceramic-thermoset polymer composite.

4. The gas heater of claim 1, wherein the resistive element is formed from a nickel based alloy.

5. The gas heater of claim 1, wherein the resistive element is constructed as a wire, a foil, a laminate, a printed ink, or a wire mesh.

6. The gas heater of claim 1, wherein the elongated tubular body is formed from UVC transparent quartz glass.

7. The gas heater of claim 1, further comprising a first sensing port for accommodating a first heat sensor adjacent the inlet port to measure an inlet gas temperature and a second sensing port for accommodating a second heat sensor adjacent the outlet port to measure an outlet gas temperature.

8. The gas heater of claim 7, wherein the first sensing port and the second sensing port are axially aligned with a longitudinal axis of the elongated tubular body.

9. The gas heater of claim 7, wherein the first sensing port and the second sensing port extend perpendicular to a longitudinal axis of the elongated tubular body.

10. The gas heater of claim 1, wherein the inlet port and the outlet port extend perpendicular to a longitudinal axis of the elongated tubular body.

11. The gas heater of claim 1, wherein electrical couplings are provided for connecting the resistive element to an electrical energy source.

12. A surgical gas delivery system comprising:
   a) a source of insufflation gas;
   b) a pressure regulator for receiving the insufflation gas from the source;
   c) an insufflation manifold for receiving pressure regulated insufflation gas from the pressure regulator for delivery to one or more surgical access ports communicating with the surgical gas delivery system; and
   d) a gas heater for heating the pressure regulated insufflation gas received by the insufflation manifold, wherein the gas heater includes:
      i) an elongated tubular body defining an interior flow passage having an inlet port for receiving the pressure regulated insufflation gas from the pressure regulator and an outlet port for delivering heated pressure regulated insufflation gas into the insufflation manifold;
      ii) a dielectric support positioned within the interior flow passage of the elongated tubular body, wherein the dielectric support is an elongated support tube defining a longitudinal axis and having an interior bore bounded by a tubular wall having an exterior surface and an interior surface, and wherein two sets of longitudinally spaced apart and diametrically opposed arcuate slots extend through the tubular wall of the elongated support tube from the exterior surface thereof to the interior surface thereof; and
      iii) a resistive element operatively associated with the dielectric support for heating the pressure regulated insufflation gas flowing through the elongated tubular body from the inlet port to the outlet port, wherein the resistive element is partially wrapped around the exterior surface of the elongated support tube and partially woven through the arcuate slots in the tubular wall of the elongated support tube, such that the resistive element extends through the interior bore of the elongated support tube to form two parallel sets of interconnected axially spaced apart sections within the interior bore of the elongated support tube that are oriented substantially transverse to the longitudinal axis of the elongated support tube and to a direction of net gas flow through the elongated tubular body.

13. The surgical gas delivery system of claim 12, further comprising a gaseous sealing manifold for communicating with a gas sealed access port and wherein the outlet port of the gas heater communicates with the gaseous sealing manifold in parallel with the insufflation manifold.

14. The surgical gas delivery system of claim 12, wherein the gas heater further includes a first sensing port accommodating a first heat sensor adjacent the inlet port to measure an inlet gas temperature and a second sensing port accommodating a second heat sensor adjacent the outlet port to measure an outlet gas temperature.

15. The surgical gas delivery system of claim 12, wherein electrical couplings are provided for connecting the resistive element of the gas heater to an electrical energy source.

16. The surgical gas delivery system of claim 12, wherein the elongated tubular body is formed from UVC transparent quartz glass, the dielectric support is formed at least in part from a ceramic material, and the resistive element is formed from a nickel based alloy.

* * * * *